(12) United States Patent     (10) Patent No.: US 11,905,243 B2
Wegert et al.     (45) Date of Patent: Feb. 20, 2024

(54) ALKYLAMINOPROLINE DERIVATIVES AS ALPHA-2-DELTA-1 BLOCKERS

(71) Applicant: ACONDICIONAMIENTO TARRASENSE, Terrassa (ES)

(72) Inventors: Anita Wegert, Aldenhoven (DE); Carmen Almansa-Rosales, Barcelona (ES)

(73) Assignee: ACONDICIONAMIENTO TARRASENSE, Barcelona (ES)

( * ) Notice: Subject to any disclaimer, the term of this patent is extended or adjusted under 35 U.S.C. 154(b) by 0 days.

(21) Appl. No.: 17/975,652

(22) Filed: Oct. 28, 2022

(65) Prior Publication Data

US 2023/0100599 A1    Mar. 30, 2023

(51) Int. Cl.
*C07D 207/16* (2006.01)

(52) U.S. Cl.
CPC .................. *C07D 207/16* (2013.01)

(58) Field of Classification Search
CPC .................................................. C07D 207/16
See application file for complete search history.

(56) References Cited

U.S. PATENT DOCUMENTS 7,300,929 B2 * 11/2007 Baxter .................. A61K 31/40
514/424

* cited by examiner

*Primary Examiner* — Kamal A Saeed
(74) *Attorney, Agent, or Firm* — Don D. Cha; HDC Intellectual Property Law, LLP

(57) ABSTRACT

The present invention relates to compounds showing pharmacological activity towards the subunit α2δ#of voltage-gated calcium channels (VGCC), especially the α2δ-1 subunit of voltage-gated calcium channels. More particularly, the invention relates to alkylaminoproline derivatives having this pharmacological activity, to processes of preparation of such compounds, to pharmaceutical compositions comprising them, and to their use in therapy, in particular for the treatment of pain and/or as neuroprotective agents.

20 Claims, No Drawings

ALKYLAMINOPROLINE DERIVATIVES AS ALPHA-2-DELTA-1 BLOCKERS

CROSS-REFERENCE TO RELATED APPLICATIONS

This application is a U.S. National Stage Patent Application under 35 U.S.C. § 371 of PCT Patent Application No. PCT/EP2021/061017, filed 27 Apr. 2021, which claims the priority benefit of EP Patent Application No. 20382342.2, filed 28 Apr. 2020, all of which are incorporated herein by reference in their entirety.

FIELD OF THE INVENTION

The present invention relates to new compounds that show pharmacological activity towards the subunit α2δ of voltage-gated calcium channels (VGCC), especially the α2δ-1 subunit of voltage-gated calcium channels.

More particularly, the present invention relates to alkylaminoproline derivatives as alfa-2-delta-1 blockers having this pharmacological activity, to processes of preparation of such compounds, to pharmaceutical compositions comprising them, and to their use in therapy, in particular for the treatment of pain and/or as neuroprotective agents.

BACKGROUND OF THE INVENTION

The adequate management of pain constitutes an important challenge, since currently available treatments provide in many cases only modest improvements, leaving many patients unrelieved (Turk, D. C., Wilson, H. D., Cahana, A.; 2011; *Lancet;* 377; 2226-2235). Pain affects a big portion of the population with an estimated prevalence of 20% and its incidence, particularly in the case of chronic pain, is increasing due to the population ageing. Additionally, pain is clearly related to comorbidities, such as depression, anxiety and insomnia, which lead to important productivity losses and socio-economical burden (Goldberg, D. S., McGee, S. J.; 2011; *BMC Public Health;* 11; 770). Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

Voltage-gated calcium channels (VGCC) are required for many key functions in the body. Different subtypes of voltage-gated calcium channels have been described (Zamponi et al., *Pharmacol. Rev.* 2015 67:821-70). The VGCC are assembled through interactions of different subunits, namely $α_1$ ($Ca_vα_1$), $β$ ($Ca_vβ$) $α_2δ$ ($Ca_vα_2δ$) and $γ$ ($Ca_vγ$). The $α_1$ subunits are the key porous forming units of the channel complex, being responsible for the $Ca^{2+}$ conduction and generation of $Ca^{2+}$ influx. The $α_2δ$, $β$, and $γ$ subunits are auxiliary, although very important for the regulation of the channel, since they increase the expression of the $α_1$ subunits in the plasma membrane as well as modulate their function, resulting in functional diversity in different cell types. Based on their physiological and pharmacological properties, VGCC can be subdivided into low voltage-activated T-type ($Ca_v3.1$, $Ca_v3.2$, and $Ca_v3.3$), and high voltage-activated L-($Ca_v1.1$ through $Ca_v1.4$), N—($Ca_v2.2$), P/Q-($Ca_v2.1$), and R—($Ca_v2.3$) types, depending on the channel forming Cava subunits. All of these five subclasses are found in the central and peripheral nervous systems. Regulation of intracellular calcium through activation of these VGCC plays obligatory roles in: 1) neurotransmitter release, 2) membrane depolarization and hyperpolarization, 3) enzyme activation and inactivation, and 4) gene regulation (Perret and Luo, Neurotherapeutics. 2009 6:679-92; Zamponi et al., 2015 supra; Neumaier et al., Prog. Neurobiol. 2015 129:1-36). A large body of data has clearly indicated that VGCC are implicated in mediating various disease states including pain processing. Drugs interacting with the different calcium channel subtypes and subunits have been developed. Current therapeutic agents include drugs targeting L-type $Ca_v1.2$ calcium channels, particularly 1,4-dihydropyridines, which are widely used in the treatment of hypertension. T-type ($Ca_v3$) channels are the target of ethosuximide, widely used in absence epilepsy. Ziconotide, a peptide blocker of N-type ($Ca_v2.2$) calcium channels, has been approved as a treatment of intractable pain. (Perret and Luo, 2009, supra; Vink and Alewood, Br J Pharmacol. 2012 167:970-89).

The $Ca_v1$ and $Ca_v2$ subfamilies contain an auxiliary $α_2δ$ subunit, which is the therapeutic target of the gabapentinoid drugs of value in certain epilepsies and chronic neuropathic pain. To date, there are four known $α_2δ$ subunits, each encoded by a unique gene and all possessing splice variants. Each $α_2δ$ protein is encoded by a single messenger RNA and is posttranslationally cleaved and then linked by disulfide bonds. Four genes encoding $α_2δ$ subunits have now been cloned. $α_2δ$-1 was initially cloned from skeletal muscle and shows a fairly ubiquitous distribution. The $α_2δ$-2 and $α_2δ$-3 subunits were subsequently cloned from brain. The most recently identified subunit, $α_2δ$-4, is largely nonneuronal. The human $α_2δ$-4 protein sequence shares 30, 32 and 61% identity with the human $α_2δ$-1, $α_2δ$-2 and $α_2δ$-3 subunits, respectively. The gene structure of all $α_2δ$ subunits is similar. All $α_2δ$ subunits show several splice variants (Davies et al., Trends Pharmacol Sci. 2007 28:220-8; Dolphin A C, Nat Rev Neurosci. 2012 13:542-55, Biochim Biophys Acta. 2013 1828:1541-9).

The $Ca_vα_2δ$-1 subunit may play an important role in neuropathic pain development (Perret and Luo, 2009, supra; Vink and Alewood, 2012, supra). Biochemical data have indicated a significant $Ca_vα_2δ$-1, but not $Ca_vα_2δ$-2, subunit upregulation in the spinal dorsal horn, and DRG (dorsal root ganglia) after nerve injury that correlates with neuropathic pain development. In addition, blocking axonal transport of injury-induced DRG $Ca_vα_2δ$-1 subunit to the central presynaptic terminals diminishes tactile allodynia in nerve injured animals, suggesting that elevated DRG $Ca_vα_2δ$-1 subunit contributes to neuropathic allodynia.

The $Ca_vα_2δ$-1 subunit (and the $Ca_vα_2δ$-2, but not $Ca_vα_2δ$-3 and $Ca_vα_2δ$-4, subunits) is the binding site for gabapentin which has anti-allodynic/hyperalgesic properties in patients and animal models. Because injury-induced $Ca_vα_2δ$-1 expression correlates with neuropathic pain development and maintenance, and various calcium channels are known to contribute to spinal synaptic neurotransmission and DRG neuron excitability, injury-induced $Ca_vα_2δ$-1 subunit upregulation may contribute to the initiation and maintenance of neuropathic pain by altering the properties and/or distribution of VGCC in the subpopulation of DRG neurons and their central terminals, therefore modulating excitability and/or synaptic neuroplasticity in the dorsal horn. Intrathecal antisense oligonucleotides against the $Ca_vα_2δ$-1 subunit can block nerve injury-induced $Ca_vα_2δ$-1 upregulation and prevent the onset of allodynia and reserve established allodynia.

As mentioned above, the $α_2δ$ subunits of VGCC form the binding site for gabapentin and pregabalin, which are structural derivatives of the inhibitory neurotransmitter GABA although they do not bind to GABAA, GABAB, or benzodiazepine receptors, or alter GABA regulation in animal brain preparations. The binding of gabapentin and pregabalin to the $Ca_v\alpha_2\delta$ subunit results in a reduction in the calcium-dependent release of multiple neurotransmitters, leading to efficacy and tolerability for neuropathic pain management. Gabapentinoids may also reduce excitability by inhibiting synaptogenesis (Perret and Luo, 2009, supra; Vink and Alewood, 2012, supra, Zamponi et al., 2015, supra).

In addition, it has been shown recently that the $\alpha_2\delta$ subunit also interacts and regulates other proteins as well as the calcium channels, such as the protein 1 related to the low-density lipoprotein receptor (LRP1), thrombospondins, α-neurexins, prion proteins, potassium channels of great conductance (BK), and NMDA receptors (Dolphin, A. C.; *F1000 Research*, 2018, 7, 1830). The regulation that the $\alpha_2\delta$ subunit exerts on these proteins suggests its involvement in new physiological, pathological and pharmacological functions. In this sense, there are numerous studies in both pre-clinical and clinical literature that reveal a possible neuroprotective role of gabapentinoids.

Neuroprotection refers to mechanisms and strategies that aim to protect the central and/or the peripheral nervous system from injury or damage, especially in people who sustain an injury or develop a health condition that has neurological effects. Nervous system disorders, injuries or trauma of various kinds to the central nervous system or the peripheral nervous system can produce serious and long-lasting neurological and/or psychiatric symptoms and disorders, through a progressive death of neurons or other cells of the central nervous system i.e., neurodegeneration. Neurodegeneration is involved in the prognosis and progression of nervous system disorders including polyneuropathy, motor neuron diseases or related disorders, movement disorders, disorders with neurocognitive impairment, cerebralvascular accidents (CVAs) stroke, injuries to the head such as, traumatic brain injury and spinal cord injuries. The neurodegenerative process in nervous system disorders constitutes an enormous medical and public health problem due to both the high incidence of these conditions and the frequency of chronic sequels.

Neuroprotection aims to prevent or slow disease progression and secondary injuries by halting or at least slowing the loss of neurons (Seidl, S. E.; Potashkin, J. A.; Frontiers in Neurology, 2011, 2, 1-19). Despite differences in symptoms or injuries associated with central nervous system disorders, many of the mechanisms behind neurodegeneration are the same. Common mechanisms include increased levels in oxidative stress, mitochondrial dysfunction, excitotoxicity, inflammatory changes, iron accumulation, and protein aggregation (Seidl, S. E.; Potashkin, J. A.; Frontiers in Neurology, 2011, 2, 1-19; Dunnet, S. B.; Bjorklun, A. Nature, 1999, 399, A32-A39; Andersen J. K. Nature Medicine, 2004, 10, S18-S25). Neuroprotective treatments to target these mechanisms include antioxidants, antiexcitotoxic agents, apoptosis inhibitors, anti-inflammatory agents, neurotrophic factors, iron chelators, stimulants, gene therapy and stem cell therapy.

Kim et al (Kim, Y. K; Leem, J. G; Sim, J. Y; Jeong, S; Joung, K. W, Korean *J. Anesthesiol.*, 2010, 58, 184-190) stated that gabapentin reduced early neuronal injury caused by focal cerebral ischemia/reperfusion in male Sprague-Dawley rats, suggesting a neuroprotective effect of gabapentin. In the same context, Yoon et al (Yoon, J. S.; Lee, J. H.; Son, T. G.; Mughal, M. R.; Greig, N. H.; Mattson, M. P. Neurobiology of Disease, 2011, 41, 624-629) demonstrated that prebabalin reduced neuronal loss and improved functional outcome in a mouse model of focal ischemic stroke. According to this data, Song et al (Song, Y.; Jun J. H.; Shin, E. J.; Kwak, Y. L.; Shin, J. S.; Shim, J. K. PLoS ONE. 2017, 12) concluded that pregabalin administration upon reperfusion conveyed significant functional and histological neuroprotection after 1 h of middle cerebral artery occlusion under hyperglycemia in male Wistar rats. These findings suggest the potential for a therapeutic benefit of pregabalin in stroke patients. Moreover, pre-clinical studies in rabbits with spinal cord ischemic injury induced by the aortic occlusion model, also demonstrated a significant neuroprotective effect of gabapentin after early phases of ischemic injury (Kale, A.; Börcek, A. O.; Emmez, H.; Yildirim, Z.; Durday, E.; Lortlar, N.; Kurt, G.; Dogulu, F.; Kilig, N. *Journal of neurosurgery*, 2011, 15, 228-237). The study of Calikoglu et al. also concluded that pregabalin had histopathological demonstrable anti-edema, anti-inflammatory, and neuroprotective effects in rats, limiting the diffuse brain damage during the acute phase of experimental brain injury. These data suggest that pregabalin may be beneficial in acute traumatic brain injury in humans via its anti-edema and anti-inflammatory actions (Calikoglu, C; Aytekin, H.; Akgül, O.; Akgül, M. H.; Gezen, A. F.; Akyuz, F.; Cakir, M. *Med Sci Monit,* 2015; 21, 813-820).

The hypotheses suggested by these preclinical studies on the neuroprotective potential of gabapentinoids have been proven by clinical studies: In a large observational cohort study, Warner et al. demonstrate that early administration of pregabalin significantly improved motor recovery following acute spinal cord injury. These effects were time dependent (within 1 month) and primarily related to the application of gabapentinoids (Warner, F. M.; Cragg, J. J.; Jutzeler, C. R.; Röhrich, F.; Weidner, N.; Saur, M.; Maier, D. D.; Schuld, C.; Curt, A.; Kramer, J. K.; *Cell Reports,* 2017, 18, 1614-1618).

Pregabalin has also shown neuroprotective effect in animal models of retinopathy and multiple sclerosis. Hundehege et al., conducted the first investigation of the putative retinal neuroprotective effect of pregabalin in an experimental model of diabetic retinopathy in Wistar rats. This study provided the first demonstration that pregabalin intervention rescued retinal cells and alleviated retinal apoptosis in diabetic rats. (Ali, S. A.; Zaitoneb, S. A.; Dessoukid, A. A.; Ali, A. A.; *Exp. Eye Res.,* 2019, 184, 70-90). Therefore, pregabalin may have a future utility in treating diabetic retinopathy after adequate clinical research. Hundehege et al. examined in an animal model of multiple sclerosis, the experimental autoimmune encephalomyelitis (EAE), whether pregabalin exerted a neuroprotective effect. The results of this study demonstrated that prophylactic and therapeutic pregabalin treatment ameliorates the course of EAE, the experimental animal model of multiple sclerosis, by directly and predominantly acting on neurons (Hundehege, P.; Fernandez-Orth, J.; Römer, P.; Ruck, T.; Müntefering, T.; Eichler, S.; Cerina, M.; Epping, L.; Albrecht, S.; Menke, A. F.; Birkner, K.; Göbel, K.; Budde, T.; Zipp, F.; Wiendla, H.; Gorji, A.; Bittner, S.; Meuth, S. G.; *Neurosignals* 2018, 26, 77-93).

The inventors have found a series of compounds that show pharmacological activity towards the $\alpha_2\delta$ subunit, in particular the $\alpha_2\delta$-1 subunit, of the voltage-gated calcium channel, resulting in an innovative, effective and alternative solution for the treatment of pain. Alternatively, these compounds can be used as innovative and effective neuroprotective agents.

In view of the existing results of the currently available therapies and clinical practices, the present invention offers a solution relevant for the treatment of pain. In addition, the present invention provides alternative neuroprotective agents. This was mainly achieved by providing the compounds according to the invention that bind to the α₂δ subunit, in particular the α₂δ-1 subunit, of the voltage-gated calcium channel.

SUMMARY OF THE INVENTION

The present invention discloses novel compounds with pharmacological activity towards the subunit α2δ of voltage-gated calcium channels (VGCC), especially the α2δ-1 subunit of voltage-gated calcium channels and to their use in therapy, in particular for the treatment of pain and pain related disorders. Alternatively, the compounds of the present invention are useful as neuroprotective agents. In particular, said neuroprotective agents are useful for the treatment of nervous system disorders concomitant with nervous system damage or nervous system injury.

The invention is directed in a main aspect to a compound of formula (I),

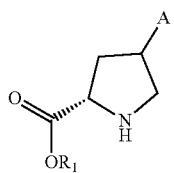

wherein R₁ and A are as defined below in the detailed description.

A further aspect of the invention refers to the processes for preparation of compounds of formula (I).

A still further aspect of the invention refers to the use of intermediate compounds for the preparation of a compound of formula (I).

It is also an aspect of the invention a pharmaceutical composition comprising a compound of formula (I).

Finally, it is an aspect of the invention a compound of formula (I) for use in therapy.

DETAILED DESCRIPTION OF THE INVENTION

The invention is directed to a family of compounds, in particular, to alkylaminoproline derivatives as α₂δ blockers which show a pharmacological activity towards the α₂δ subunit, in particular the α₂δ-1 subunit, of the voltage-gated calcium channel thus, solving the above problems of identifying alternative or improved pain treatments and/or providing alternative neuroprotective agents by offering such compounds.

The applicant has found that the problem of providing a new effective and alternative solution for treating pain and pain related disorders can surprisingly be solved by using an analgesic approach using compounds binding to the α₂S subunit, in particular the α₂δ-1 subunit, of the voltage-gated calcium channel. Further, the applicant has found that these compounds are useful as neuroprotective agents. In particular, said neuroprotective agents are useful for the treatment of nervous system disorders concomitant with nervous system damage or nervous system injury.

In a first aspect, the present invention is directed to a compound of formula (I):

wherein
R₁ is selected from the group consisting of hydrogen, unsubstituted or substituted C₁₋₆ alkyl, substituted or unsubstituted C₂₋₆ alkenyl, and substituted or unsubstituted C₂₋₆ alkynyl;
A is —(CH₂)ₙ—NR₂R₂', wherein
n is 0, 1 or 2;
R₂ is unsubstituted C₁₋₆ alkyl; and
R₂' is —(CH₂)ₘ—R₃, wherein
m is 0, 1, 2 or 3;
R₃ is selected from the group consisting of unsubstituted or substituted aryl, unsubstituted or substituted cycloalkyl, and unsubstituted or substituted heterocyclyl, wherein the heterocyclyl is not a sulfur-containing heterocyclyl;
wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

The compounds of the invention represented by the above described formula (I) may include enantiomers depending on the presence of chiral centres or isomers depending on the presence of multiple bonds. The single isomers, enantiomers or diastereoisomers and mixtures thereof fall within the scope of the present invention.

In another embodiment, these compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt or solvate thereof.

For the sake of clarity the expression "a compound according to formula (I), wherein R₁ and A are as defined below in the detailed description" would (just like the expression "a compound of formula (I) as defined in any one of the claims) refer to "a compound according to formula (I)", wherein the definitions of the respective substituents R₁ etc. (also from the cited claims) are applied.

For clarity purposes, all groups and definitions described in the present description and referring to compounds of formula (I), also apply to all intermediates of synthesis.

In connection with alkyl (also in alkyl-heterocyclyl, alkyl-cycloalkyl or alkyl-aryl), alkenyl, alkynyl and O-alkyl—unless defined otherwise—the term substituted in the context of this invention is understood as meaning replacement of at least one hydrogen radical on a carbon atom by halogen, —OR', —SR', —SOR', —SO₂R', —OR', —CN, —COR', —COOR', —NR'R", —CONR'R", haloalkyl, haloalkoxy or —OC₁₋₆ alkyl wherein each of the R' and R" groups is independently selected from the group consisting of hydrogen, OH, NO₂, NH₂, SH, CN, halogen, —COH, —COalkyl, —COOH and C₁₋₆ alkyl.

More particularly, the alkyl, alkenyl or alkynyl as defined in $R_1$ or $R_2$ if substituted, is substituted with one or more substituent/s selected from —OR', halogen, —CN, haloalkyl, haloalkoxy and —NR'R"; wherein R' and R" are independently selected from hydrogen, unsubstituted $C_{1-6}$ alkyl, unsubstituted $C_{2-6}$ alkenyl, and unsubstituted $C_{2-6}$ alkynyl.

More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. —CH(OH)—CH═CH—CHCl$_2$.

In the context of this invention haloalkyl is understood as meaning an alkyl being substituted once or several times by a halogen (selected from F, Cl, Br, I). It encompasses e.g. —CH$_2$Cl, —CH$_2$F, —CHCl$_2$, —CHF$_2$, —CCl$_3$, —CF$_3$ and —CH$_2$—CHCl$_2$. Preferably haloalkyl is understood in the context of this invention as halogen-substituted $C_{1-4}$-alkyl representing halogen substituted C1-, C2-, C3- or C4-alkyl. The halogen-substituted alkyl radicals are thus preferably methyl, ethyl, propyl, and butyl. Preferred examples include —CH$_2$Cl, —CH$_2$F, —CH$_2$—CH$_2$F, —CH$_2$—CHF$_2$, —CHCl$_2$, —CHF$_2$, and —CF$_3$.

In the context of this invention haloalkoxy is understood as meaning an —O-alkyl being substituted once or several times by a halogen (selected from F, C, Br, I). It encompasses e.g. —OCH$_2$Cl, —OCH$_2$F, —OCHCl$_2$, —OCHF$_2$, —OCC$_3$, —OCF$_3$ and —OCH$_2$—CHCl$_2$. Preferably haloalkoxy is understood in the context of this invention as halogen-substituted —OC$_{1-4}$-alkyl representing halogen substituted C1-, C2-, C3- or C4-alkoxy. The halogen-substituted O-alkyl radicals are thus preferably O-methyl, O-ethyl, O-propyl, and O-butyl. Preferred examples include —OCH$_2$Cl, —OCH$_2$F, —OCHCl$_2$, —OCHF$_2$, and —OCF$_3$.

In the context of this invention cycloalkyl is understood as meaning saturated and unsaturated (but not aromatic) cyclic hydrocarbons (without a heteroatom in the ring), which can be unsubstituted or once or several times substituted. Preferred cycloalkyls are $C_{3-4}$-cycloalkyl representing C3- or C4-cycloalkyl, $C_{3-5}$-cycloalkyl representing C3-, C4- or C5-cycloalkyl, $C_{3-6}$-cycloalkyl representing C3-, C4-, C5- or C6-cycloalkyl, $C_{3-7}$-cycloalkyl representing C3-, C4-, C5-, C6- or C7-cycloalkyl, $C_{3-8}$-cycloalkyl representing C3-, C4-, C5-, C6-, C7- or C8-cycloalkyl, $C_{4-5}$-cycloalkyl representing C4- or C5-cycloalkyl, $C_{4-6}$-cycloalkyl representing C4-, C5- or C6-cycloalkyl, $C_{4-7}$-cycloalkyl representing C4-, C5-, C6- or C7-cycloalkyl, $C_{5-6}$-cycloalkyl representing C5- or C6-cycloalkyl and $C_{5-7}$-cycloalkyl representing C5-, C6- or C7-cycloalkyl. Examples are cyclopropyl, 2-methylcyclopropyl, cyclopropylmethyl, cyclobutyl, cyclopentyl, cyclopentylmethyl, cyclohexyl, cycloheptyl, cyclooctyl, and also adamantyl. Preferably in the context of this invention cycloalkyl is $C_{3-8}$-cycloalkyl like cyclopropyl, cyclobutyl, cyclopentyl, cyclohexyl, cycloheptyl, or cyclooctyl; or is $C_{3-7}$-cycloalkyl like cyclopropyl, cyclobutyl, cyclopentyl, cyclohexyl, or cycloheptyl; or is $C_{3-6}$-cycloalkyl like cyclopropyl, cyclobutyl, cyclopentyl or cyclohexyl, especially cyclopentyl or cyclohexyl.

Aryl is understood as meaning 6 to 18 membered mono or polycyclic ring systems with at least one aromatic ring but without heteroatoms even in only one of the rings. Examples are phenyl, naphthyl, fluoranthenyl, fluorenyl, tetralinyl or indanyl, 9H-fluorenyl or anthracenyl radicals, which can be unsubstituted or once or several times substituted. Most preferably aryl is understood in the context of this invention as phenyl, naphthyl or anthracenyl, more preferably the aryl is phenyl.

A heterocyclyl radical or group (also called heterocyclyl hereinafter) is understood as meaning 5 to 18 membered mono or polycyclic heterocyclic ring systems, with at least one saturated or unsaturated ring which contains one or more heteroatoms selected from the group consisting of nitrogen, oxygen and/or sulfur in the ring. A heterocyclic group can also be substituted once or several times.

Examples include non-aromatic heterocyclyls such as tetrahydropyran, oxazepane, morpholine, piperidine, pyrrolidine as well as heteroaryls such as furan, benzofuran, thiophene, benzothiophene, pyrrole, pyridine, pyrimidine, pyrazine, quinoline, isoquinoline, phthalazine, thiazole, benzothiazole, indole, benzotriazole, carbazole and quinazoline.

Subgroups inside the heterocyclyls as understood herein include heteroaryls and non-aromatic heterocyclyls.

the heteroaryl (being equivalent to heteroaromatic radicals or aromatic heterocyclyls) is an aromatic 5 to 18 membered mono or polycyclic heterocyclic ring system of one or more rings of which at least one aromatic ring contains one or more heteroatoms from the group consisting of nitrogen, oxygen and/or sulfur in the ring; preferably is a 5 to 18 membered mono or polycyclic aromatic heterocyclic ring system of one or two rings of which at least one aromatic ring contains one or more heteroatoms selected from the group consisting of nitrogen, oxygen and/or sulfur in the ring, more preferably it is selected from furan, benzofuran, thiophene, benzothiophene, pyrrole, pyridine, pyrimidine, pyrazine, quinoline, isoquinoline, phthalazine, benzothiazole, indole, benzotriazole, carbazole, quinazoline, thiazole, imidazole, pyrazole, oxazole, thiophene and benzimidazole;

the non-aromatic heterocyclyl is a 5 to 18 membered mono or polycyclic heterocyclic ring system of one or more rings of which at least one ring—with this (or these) ring(s) then not being aromatic—contains one or more heteroatoms from the group consisting of nitrogen, oxygen and/or sulfur in the ring; preferably it is a 5 to 18 membered mono or polycyclic heterocyclic ring system of one or two rings of which one or both rings—with this one or two rings then not being aromatic—contain/s one or more heteroatoms selected from the group consisting of nitrogen and oxygen in the ring, more preferably it is selected from oxazepane, pyrrolidine, piperidine, piperazine, tetrahydropyran, morpholine, indoline, oxopyrrolidine, benzodioxane.

Preferably, in the context of this invention heterocyclyl is defined as a 5 to 18 membered mono or polycyclic ring system of one or more saturated or unsaturated rings of which at least one ring contains one or more heteroatoms selected from the group consisting of nitrogen and/or oxygen in the ring. Preferably it is a 5 to 18 membered mono or polycyclic heterocyclic ring system of one or two saturated or unsaturated rings of which at least one ring contains one or more heteroatoms selected from the group consisting of nitrogen and/or oxygen in the ring. In another preferred embodiment of the invention, said heterocyclyl is a substituted mono or bicyclic heterocyclyl ring system.

Preferred examples of heterocyclyls include oxazepane, pyrrolidine, imidazole, oxadiazole, tetrazole, pyridine, pyrimidine, piperidine, piperazine, benzofuran, benzimidazole, indazole, benzodiazole, benzothiazole, tetrahydropyran, morpholine, indoline, furan, isoxazole, pyrazole, pyrrole, pyrazine, pyrrolo[2,3b]pyridine, quinoline, isoquinoline, tetrahydroisoquinoline, phthalazine, indole, benzoxazole, oxopyrrolidine, pyrimidine, benzodioxolane, benzodioxane, carbazole and quinazoline, especially is pyridine, piperazine, pyrazine, indazole, benzodioxane, morpholine, tetrahydropyran, pyrazole, imidazole, piperidine, indole, benzimidazole, pyrrolo[2,3b]pyridine, benzoxazole, oxopyrrolidine, pyrimidine, oxazepane and pyrrolidine. In the context of this invention oxopyrrolidine is understood as meaning pyrrolidin-2-one.

In connection with aromatic heterocyclyls (heteroaryls), non-aromatic heterocyclyls, aryls and cycloalkyls, when a ring system falls within two or more of the above cycle definitions simultaneously, then the ring system is defined first as an aromatic heterocyclyl (heteroaryl) if at least one aromatic ring contains a heteroatom. If no aromatic ring contains a heteroatom, then the ring system is defined as a non-aromatic heterocyclyl if at least one non-aromatic ring contains a heteroatom. If no non-aromatic ring contains a heteroatom, then the ring system is defined as an aryl if it contains at least one aryl cycle. If no aryl is present, then the ring system is defined as a cycloalkyl if at least one non-aromatic cyclic hydrocarbon is present.

In the context of this invention alkyl-aryl is understood as meaning an aryl group (see above) being connected to another atom through a $C_{1-6}$-alkyl (see above) which may be branched or linear and is unsubstituted or substituted once or several times as described before. Preferably aryl-alkyl is understood as meaning an aryl group (see above) being connected to another atom through 1 to 4 (—$CH_2$—) groups.

In the context of this invention alkyl-heterocyclyl is understood as meaning an heterocyclyl group (see above) being connected to another atom through a $C_{1-6}$-alkyl (see above) which may be branched or linear and is unsubstituted or substituted once or several times as described before. Preferably alkyl-heterocyclyl is understood as meaning an heterocyclyl group (see above) being connected to another atom through 1 to 4 (—$CH_2$—) groups.

In the context of this invention alkyl-cycloalkyl is understood as meaning a cycloalkyl group (see above) being connected to another atom through a $C_{1-6}$-alkyl (see above) which may be branched or linear and is unsubstituted or substituted once or several times as described before. Preferably alkylcycloalkyl is understood as meaning a cycloalkyl group (see above) being connected to another atom through 1 to 4 (—$CH_2$—) groups.

Preferably, the aryl is a monocyclic aryl. More preferably the aryl is a 6 or 7 membered monocyclic aryl. Even more preferably the aryl is a 6 membered monocyclic aryl, preferably phenyl.

Preferably, the heteroaryl is a monocyclic heteroaryl. More preferably the heteroaryl is a 5, 6 or 7 membered monocyclic heteroaryl. Even more preferably the heteroaryl is a 5 or 6 membered monocyclic heteroaryl.

Preferably, the non-aromatic heterocyclyl is a monocyclic non-aromatic heterocyclyl. More preferably the non-aromatic heterocyclyl is a 4, 5, 6 or 7 membered monocyclic non-aromatic heterocyclyl. Even more preferably the non-aromatic heterocyclyl is a 5 or 6 membered monocyclic non-aromatic heterocyclyl.

Preferably, the cycloalkyl is a monocyclic cycloalkyl. More preferably the cycloalkyl is a 3, 4, 5, 6, 7 or 8 membered monocyclic cycloalkyl. Even more preferably the cycloalkyl is a 3, 4, 5 or 6 membered monocyclic cycloalkyl.

A ring system is a system consisting of at least one ring of connected atoms but including also systems in which two or more rings of connected atoms are joined with "joined" meaning that the respective rings are sharing one (like a spiro structure), two or more atoms being a member or members of both joined rings.

The term "leaving group" means a molecular fragment that departs with a pair of electrons in heterolytic bond cleavage. Leaving groups can be anions or neutral molecules. Common anionic leaving groups are halides such as Cl—, Br—, and I—, and sulfonate esters, such as tosylate (TsO—), mesylate, nosylate or triflate.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes via ionic interactions. The definition particularly includes physiologically acceptable salts, this term must be understood as equivalent to "pharmacologically acceptable salts".

The term "physiologically acceptable salt" means in the context of this invention any salt that is physiologically tolerated (most of the time meaning not being toxic-especially lacking toxicity caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with $NH_4$, but in particular (mono)- or (di)sodium, (mono)- or (di)potassium, magnesium or calcium salts.

Physiologically acceptable salts can also be formed with anions or acids and in the context of this invention is understood as meaning salts of at least one of the compounds used according to the invention as the cation with at least one anion which are physiologically tolerated—especially if used on humans and/or mammals. By this it is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be present in crystalline form or in the form of free compounds like a free base or acid.

Any compound that is a solvate of a compound according to the invention like a compound according to formula (I) defined above is understood to be also covered by the scope of the invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent). Especially preferred examples include hydrates and alcoholates, like methanolates or ethanolates.

Any compound that is a prodrug of a compound according to the invention like a compound according to formula (I) defined above is understood to be also covered by the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of methods of producing a prodrug of a given acting compound are known to those skilled in the art and can be found e.g. in Krogsgaard-Larsen et al. "Textbook of Drug design and Discovery" Taylor & Francis (April 2002).

Any compound that is a N-oxide of a compound according to the invention like a compound according to formula (I) defined above is understood to be also covered by the scope of the invention.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon or of a nitrogen by $^{15}N$-enriched nitrogen are within the scope of this invention.

The compounds of formula (I) as well as their salts or solvates are preferably in pharmaceutically acceptable or substantially pure form. By pharmaceutically acceptable pure form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts. This applies also to its solvates or prodrugs.

All the groups above mentioned that can be substituted or unsubstituted may be substituted—unless defined otherwise—at one or more available positions by one or more suitable groups such as OR', =O, SR', SOR', SO$_2$R', OSO$_2$R', OSO$_3$R', NO$_2$, NHR', N(R')$_2$, =N—R', N(R')COR', N(COR')$_2$, N(R')SO$_2$R', N(R')C(=NR')N(R')R', N$_3$, CN, halogen, COR', COOR', OCOR', OCOOR', OCONHR', OCON(R')$_2$, CONHR', CON(R')$_2$, CON(R')OR', CON(R') SO$_2$R', PO(OR')$_2$, PO(OR')R', PO(OR')(N(R')R'), C$_{1-12}$ alkyl, C$_{3-10}$ cycloalkyl, C$_{2-12}$ alkenyl, C$_{2-12}$ alkynyl, aryl, and heterocyclic group, wherein each of the R' groups is independently selected from the group consisting of hydrogen, OH, NO$_2$, NH$_2$, SH, CN, halogen, COH, COalkyl, COOH, C$_{1-12}$ alkyl, C$_{3-10}$ cycloalkyl, C$_{2-12}$ alkenyl, C$_{2-12}$ alkynyl, aryl and heterocyclic group. Where such groups are themselves substituted, the substituents may be chosen from the foregoing list.

In a preferred embodiment of the invention, the compound of formula (I) according to the invention is a compound wherein R$_1$ is hydrogen (Ia);

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another particular embodiment, the invention refers to a compound of formula (Ib):

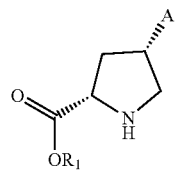

(Ib)

wherein
R$_1$ is selected from the group consisting of hydrogen, unsubstituted or substituted C$_{1-6}$ alkyl, substituted or unsubstituted C$_{2-6}$ alkenyl, and substituted or unsubstituted C$_{2-6}$ alkynyl; preferably, R$_1$ is hydrogen;
A is —(CH$_2$)$_n$—NR$_2$R$_2$', wherein
n is 0, 1 or 2;
R$_2$ is unsubstituted C$_{1-6}$ alkyl; and
R$_2$' is —(CH$_2$)$_m$—R$_3$, wherein
m is 0, 1, 2 or 3;
R$_3$ is selected from the group consisting of unsubstituted or substituted aryl, unsubstituted or substituted cycloalkyl, and unsubstituted or substituted heterocyclyl, wherein the heterocyclyl is not a S-containing heterocyclyl;
wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another particular embodiment of the invention, the compound of formula (I) according to the invention is a compound wherein
R$_2$ is unsubstituted C$_{1-3}$ alkyl; preferably unsubstituted methyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another particular embodiment of the invention, the compound of formula (I) according to the invention is a compound wherein
R$_2$' is —(CH$_2$)$_m$—R$_3$, wherein
m is 0, 1, 2 or 3; preferably m is 0 or 1; more preferably m is 1;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another particular embodiment of the invention, the compound of formula (I) according to the invention is a compound wherein
R$_3$ is unsubstituted or substituted aryl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In the context of the invention, when the aryl, heterocyclyl or cycloalkyl in R$_3$ is substituted, the substituents are selected from halogen, unsubstituted C$_{1-6}$ alkyl, —OR', —SR', —SOR', —SO$_2$R', —CN, —COR', —COOR', haloalkyl, haloalkoxy or —OC$_{1-6}$ alkyl wherein R' is selected from the group consisting of hydrogen, OH and unsubstituted C$_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment, when the aryl in R$_3$ is substituted, the substituent is halogen, preferably said halogen is fluorine, bromine or chlorine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another particular embodiment of the invention, the compound of formula (I) according to the invention is a compound wherein m is 0, 1 or 2; preferably, m is 1;

wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another particular embodiment of the invention, the compound of formula (I) according to the invention is a compound wherein n is 0, 1 or 2; preferably, n is 0 or 1;

wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another particular embodiment of the invention, the compound of formula (I) according to the invention is a compound wherein A is —(CH$_2$)$_n$—NR$_2$R$_2$', wherein
n is 0 or 1;
R$_2$ is unsubstituted C$_{1-6}$ alkyl; preferably unsubstituted C$_{1-3}$ alkyl; and
R$_2$' is —(CH$_2$)$_m$—R$_3$, wherein
m is 0, 1 or 2; preferably m is 0 or 1; and
R$_3$ is selected from the group consisting of unsubstituted or substituted aryl, unsubstituted or substituted cycloalkyl, and unsubstituted or substituted heterocyclyl, wherein the heterocyclyl is not a sulfur-containing heterocyclyl;

wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a more particular embodiment of the invention, the compound of formula (I) according to the invention is a compound wherein A is —(CH$_2$)$_n$—NR$_2$R$_2$', wherein
n is 0 or 1;
R$_2$ is unsubstituted C$_{1-3}$ alkyl; preferably methyl; and
R$_2$' is —(CH$_2$)$_m$—R$_3$, wherein
m is 0 or 1; and
R$_3$ is selected from the group consisting of unsubstituted or substituted aryl;

wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the invention, the compound of formula (I) according to the invention is a compound wherein A is —(CH$_2$)$_n$—NR$_2$R$_2$', wherein
n is 0;
R$_2$ is unsubstituted C$_{1-3}$ alkyl; preferably methyl; and
R$_2$' is —(CH$_2$)$_m$—R$_3$, wherein
m is 1; and
R$_3$ is selected from the group consisting of unsubstituted or substituted aryl;

wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a more preferred embodiment of the invention, the compound of formula (I) according to the invention is a compound wherein A is —(CH$_2$)$_n$—NR$_2$R$_2$', wherein
n is 0;
R$_2$ is unsubstituted C$_{1-3}$ alkyl; preferably methyl; and
R$_2$' is —(CH$_2$)$_m$—R$_3$, wherein
m is 1; and
R$_3$ is unsubstituted aryl; preferably phenyl;

wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention, the compound of formula (I) according to the invention is a compound wherein A is —(CH$_2$)$_n$—NR$_2$R$_2$', wherein
n is 0;
R$_2$ is unsubstituted C$_{1-3}$ alkyl; preferably methyl; and
R$_2$' is —(CH$_2$)$_m$—R$_3$, wherein
m is 0; and
R$_3$ is selected from the group consisting of unsubstituted or substituted aryl;

wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the invention, the compound of formula (I) according to the invention is a compound wherein A is —(CH$_2$)$_n$—NR$_2$R$_2$', wherein
n is 1;
R$_2$ is unsubstituted C$_{1-3}$ alkyl; preferably methyl; and
R$_2$' is —(CH$_2$)$_m$—R$_3$, wherein
m is 0; and
R$_3$ is selected from the group consisting of unsubstituted or substituted aryl;

wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention, the compound of formula (I) according to the invention is a compound wherein
A is —$(CH_2)_n$—$NR_2R_2'$, wherein
n is 1;
$R_2$ is unsubstituted $C_{1-3}$ alkyl; preferably methyl; and
$R_2'$ is —$(CH_2)_m$—$R_3$, wherein
m is 0; and
$R_3$ is unsubstituted aryl, preferably phenyl;
wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to formula (I) the compound is a compound, wherein in $R_1$ as defined in any of the embodiments of the present invention,
the $C_{1-6}$alkyl is preferably selected from methyl, ethyl, propyl, butyl, pentyl, hexyl, isopropyl, and 2-methylpropyl;
and/or
the $C_{2-6}$-alkenyl is preferably selected from ethylene, propylene, butylene, pentylene, hexylene, isopropylene, and isobutylene;
and/or
the $C_{2-6}$-alkynyl is preferably selected from ethyne, propyne, butyne, pentyne, hexyne, isopropyne, and isobutyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to formula (I) the compound is a compound, wherein in $R_2$ as defined in any of the embodiments of the present invention,
the $C_{1-6}$alkyl is preferably selected from methyl, ethyl, propyl, butyl, pentyl, hexyl, isopropyl, and 2-methylpropyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to formula (I) the compound is a compound, wherein in $R_3$ as defined in any of the embodiments of the present invention,
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
and/or
the aryl is selected from phenyl, naphthyl, or anthracene; preferably is naphthyl and phenyl;
and/or the heterocyclyl is a heterocyclic ring system of one or more saturated or unsaturated rings of which at least one ring contains one or more heteroatoms; preferably, the heterocyclyl is not a sulfur-containing heterocyclyl. More preferably, the heteroatoms in the ring are selected from the group consisting of nitrogen and/or oxygen; preferably is a heterocyclic ring system of one or two saturated or unsaturated rings of which at least one ring contains one or more heteroatoms selected from the group consisting of nitrogen and/or oxygen, more preferably is selected from oxazepane, pyrrolidine, imidazole, oxadiazole, tetrazole, pyridine, pyrimidine, piperidine, piperazine, benzofuran, benzimidazole, indazole, benzodiazole, tetrahydropyran, morpholine, indoline, furan, isoxazole, pyrazole, pyrrole, pyrazine, pyrrolo[2,3b]pyridine, quinoline, isoquinoline, phthalazine, indole, benzoxazole oxopyrrolidine, pyrimidine, benzodioxolane, benzodioxane, carbazole, and quinazoline; more preferably is piperazine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment, the compound of the invention according to formula (I) is a compound, wherein
$R_1$ is selected from the group consisting of hydrogen, unsubstituted or substituted $C_{1-6}$ alkyl, substituted or unsubstituted $C_{2-6}$ alkenyl, and substituted or unsubstituted $C_{2-6}$ alkynyl; preferably, $R_1$ is hydrogen;
and/or
A is —$(CH_2)_n$—$NR_2R_2'$, wherein
n is 0, 1 or 2;
and/or
$R_2$ is unsubstituted $C_{1-6}$ alkyl; and
$R_2'$ is —$(CH_2)_m$—$R_3$, wherein
m is 0, 1, 2 or 3;
and/or
$R_3$ is selected from the group consisting of unsubstituted or substituted aryl, unsubstituted or substituted cycloalkyl, and unsubstituted or substituted heterocyclyl, wherein the heterocyclyl is not a sulfur-containing heterocyclyl;
wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment, the compound of the invention according to formula (I) is a compound, wherein
$R_1$ is selected from the group consisting of hydrogen, unsubstituted or substituted $C_{1-6}$ alkyl, substituted or unsubstituted $C_{2-6}$ alkenyl, and substituted or unsubstituted $C_{2-6}$ alkynyl; preferably, $R_1$ is hydrogen;
and/or
A is —$(CH_2)_n$—$NR_2R_2'$, wherein
n is 0 or 1;
and/or
$R_2$ is unsubstituted $C_{1-6}$ alkyl; preferably unsubstituted $C_{1-3}$ alkyl; and
$R_2'$ is —$(CH_2)_m$—$R_3$, wherein
m is 0, 1 or 2; preferably m is 0 or 1;
and/or R$_3$ is selected from the group consisting of unsubstituted or substituted aryl, unsubstituted or substituted cycloalkyl, and unsubstituted or substituted heterocyclyl, wherein the heterocyclyl is not a sulfur-containing heterocyclyl;

wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a more particular embodiment of the invention, the compound of formula (I) according to the invention is a compound wherein R$_1$ is selected from the group consisting of hydrogen, unsubstituted or substituted C$_{1-6}$ alkyl, substituted or unsubstituted C$_{2-6}$ alkenyl, and substituted or unsubstituted C$_{2-6}$ alkynyl; preferably, R$_1$ is hydrogen;

and/or

A is —(CH$_2$)$_n$—NR$_2$R$_2$', wherein
n is 0 or 1;
and/or
R$_2$ is unsubstituted C$_{1-3}$ alkyl; preferably methyl; and
R$_2$' is —(CH$_2$)$_m$—R$_3$, wherein
m is 0 or 1;
and/or
R$_3$ is selected from the group consisting of unsubstituted or substituted aryl;

wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the invention, the compound of formula (I) according to the invention is a compound wherein R$_1$ is selected from the group consisting of hydrogen, unsubstituted or substituted C$_{1-6}$ alkyl, substituted or unsubstituted C$_{2-6}$ alkenyl, and substituted or unsubstituted C$_{2-6}$ alkynyl; preferably, R$_1$ is hydrogen;

and/or

A is —(CH$_2$)$_n$—NR$_2$R$_2$', wherein
n is 0;
and/or
R$_2$ is unsubstituted C$_{1-3}$ alkyl; preferably methyl; and
R$_2$' is —(CH$_2$)$_m$—R$_3$, wherein
m is 1;
and/or
R$_3$ is selected from the group consisting of unsubstituted or substituted aryl;

wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a more preferred embodiment of the invention, the compound of formula (I) according to the invention is a compound wherein R$_1$ is hydrogen;
and/or
A is —(CH$_2$)$_n$—NR$_2$R$_2$', wherein
n is 0;
and/or
R$_2$ is unsubstituted C$_{1-3}$ alkyl; preferably methyl; and
R$_2$' is —(CH$_2$)$_m$—R$_3$, wherein
m is 1;
and/or
R$_3$ is unsubstituted aryl; preferably phenyl;

wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention, the compound of formula (I) according to the invention is a compound wherein R$_1$ is hydrogen;
and/or
A is —(CH$_2$)$_n$—NR$_2$R$_2$', wherein
n is 0;
and/or
R$_2$ is unsubstituted C$_{1-3}$alkyl; preferably methyl; and
R$_2$' is —(CH$_2$)$_m$—R$_3$, wherein
m is 0;
and/or
R$_3$ is selected from the group consisting of unsubstituted or substituted aryl;

wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the invention, the compound of formula (I) according to the invention is a compound wherein R$_1$ is hydrogen;
and/or
A is —(CH$_2$)$_n$—NR$_2$R$_2$', wherein
n is 1;
and/or
R$_2$ is unsubstituted C$_{1-3}$ alkyl; preferably methyl; and
R$_2$' is —(CH$_2$)$_m$—R$_3$, wherein
m is 0;
and/or
R$_3$ is selected from the group consisting of unsubstituted or substituted aryl;

wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention, the compound of formula (I) according to the invention is a compound wherein R$_1$ is hydrogen;
and/or
A is —(CH$_2$)$_n$—NR$_2$R$_2$', wherein
n is 1;
and/or
R$_2$ is unsubstituted C$_{1-3}$ alkyl; preferably methyl; and
R$_2$' is —(CH$_2$)$_m$—R$_3$, wherein
m is 0;
and/or
R$_3$ is selected from the group consisting of unsubstituted aryl, preferably phenyl;

wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment, the compound of the invention according to formula (I) is a compound, wherein $R_1$ is selected from the group consisting of hydrogen, unsubstituted or substituted $C_{1-6}$ alkyl, substituted or unsubstituted $C_{2-6}$ alkenyl, and substituted or unsubstituted $C_{2-6}$ alkynyl; preferably, $R_1$ is hydrogen;
and
A is —$(CH_2)_n$—$NR_2R_2'$, wherein
n is 0, 1 or 2;
and
$R_2$ is unsubstituted $C_{1-6}$ alkyl; and
$R_2'$ is —$(CH_2)_m$—$R_3$, wherein
m is 0, 1, 2 or 3;
and
$R_3$ is selected from the group consisting of unsubstituted or substituted aryl, unsubstituted or substituted cycloalkyl, and unsubstituted or substituted heterocyclyl, wherein the heterocyclyl is not a sulfur-containing heterocyclyl;
wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment, the compound of the invention according to formula (I) is a compound, wherein $R_1$ is selected from the group consisting of hydrogen, unsubstituted or substituted $C_{1-6}$ alkyl, substituted or unsubstituted $C_{2-6}$ alkenyl, and substituted or unsubstituted $C_{2-6}$ alkynyl; preferably, $R_1$ is hydrogen;
and
A is —$(CH_2)_n$—$NR_2R_2'$, wherein
n is 0 or 1;
and
$R_2$ is unsubstituted $C_{1-6}$ alkyl; preferably unsubstituted $C_{1-3}$ alkyl; and
$R_2'$ is —$(CH_2)_m$—$R_3$, wherein
m is 0, 1 or 2; preferably m is 0 or 1;
and
$R_3$ is selected from the group consisting of unsubstituted or substituted aryl, unsubstituted or substituted cycloalkyl, and unsubstituted or substituted heterocyclyl, wherein the heterocyclyl is not a sulfur-containing heterocyclyl;
wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a more particular embodiment of the invention, the compound of formula (I) according to the invention is a compound wherein $R_1$ is selected from the group consisting of hydrogen, unsubstituted or substituted $C_{1-6}$ alkyl, substituted or unsubstituted $C_{2-6}$ alkenyl, and substituted or unsubstituted $C_{2-6}$ alkynyl; preferably, $R_1$ is hydrogen;
and
A is —$(CH_2)_n$—$NR_2R_2'$, wherein
n is 0 or 1;
and
$R_2$ is unsubstituted $C_{1-3}$ alkyl; preferably methyl; and
$R_2'$ is —$(CH_2)_m$—$R_3$, wherein
m is 0 or 1;
and
$R_3$ is selected from the group consisting of unsubstituted or substituted aryl;
wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the invention, the compound of formula (I) according to the invention is a compound wherein $R_1$ is selected from the group consisting of hydrogen, unsubstituted or substituted $C_{1-6}$ alkyl, substituted or unsubstituted $C_{2-6}$ alkenyl, and substituted or unsubstituted $C_{2-6}$ alkynyl; preferably, $R_1$ is hydrogen;
and
A is —$(CH_2)_n$—$NR_2R_2'$, wherein
n is 0;
and
$R_2$ is unsubstituted $C_{1-3}$ alkyl; preferably methyl; and
$R_2'$ is —$(CH_2)_m$—$R_3$, wherein
m is 1;
and
$R_3$ is selected from the group consisting of unsubstituted or substituted aryl;
wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a more preferred embodiment of the invention, the compound of formula (I) according to the invention is a compound wherein $R_1$ is hydrogen;
and
A is —$(CH_2)_n$—$NR_2R_2'$, wherein
n is 0;
and
$R_2$ is unsubstituted $C_{1-3}$ alkyl; preferably methyl; and
$R_2'$ is —$(CH_2)_m$—$R_3$, wherein
m is 1;
and
$R_3$ is unsubstituted aryl; preferably phenyl;
wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention, the compound of formula (I) according to the invention is a compound wherein $R_1$ is hydrogen;
and
A is —$(CH_2)_n$—$NR_2R_2'$, wherein
n is 0;
and
$R_2$ is unsubstituted $C_{1-3}$ alkyl; preferably methyl; and
$R_2'$ is —$(CH_2)_m$—$R_3$, wherein
m is 0;
and
$R_3$ is selected from the group consisting of unsubstituted or substituted aryl;
wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the invention, the compound of formula (I) according to the invention is a compound wherein $R_1$ is hydrogen;
A is —$(CH_2)_n$—$NR_2R_2'$, wherein
n is 1;
and
$R_2$ is unsubstituted $C_{1-3}$ alkyl; preferably methyl; and
$R_2'$ is —$(CH_2)_m$—$R_3$, wherein
m is 0;
and
$R_3$ is selected from the group consisting of unsubstituted or substituted aryl;

wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention, the compound of formula (I) according to the invention is a compound wherein $R_1$ is hydrogen;
A is —$(CH_2)_n$—$NR_2R_2'$, wherein
n is 1;
and
$R_2$ is unsubstituted $C_{1-3}$alkyl; preferably methyl; and
$R_2'$ is —$(CH_2)_m$—$R_3$, wherein
m is 0;
and
$R_3$ is selected from the group consisting of unsubstituted aryl, preferably phenyl;

wherein the compound of formula (I) is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred further embodiment, the compound of formula (I) is selected from the group consisting of:
[1] (2S,4S)-4-(Benzyl(methyl)amino)pyrrolidine-2-carboxylic acid;
[2] (2S,4S)-4-((3-Chlorobenzyl)(methyl)amino)pyrrolidine-2-carboxylic acid;
[3] (2S,4S)-4-((4-Fluorobenzyl)(methyl)amino)pyrrolidine-2-carboxylic acid;
[4] (2S,4S)-4-((2-Fluorobenzyl)(methyl)amino)pyrrolidine-2-carboxylic acid;
[5] (2S,4S)-4-((2,4-Difluorobenzyl)(methyl)amino)pyrrolidine-2-carboxylic acid;
[6] (2S,4S)-4-((3,4-Difluorobenzyl)(methyl)amino)pyrrolidine-2-carboxylic acid;
[7] (2S,4S)-4-((Methyl(phenyl)amino)methyl)pyrrolidine-2-carboxylic acid; and
[8] (2S,4S)-4-((3-Chlorophenyl)(methyl)amino)pyrrolidine-2-carboxylic acid;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment, the compounds which are selected act as ligands of the α2δ subunit, particularly the α2δ-1 subunit, of the voltage-gated calcium channel, and especially compounds which have a binding expressed as $K_i$ (affinity value) responding to the following scales:

$K_i$(α2δ-1) is preferably <10000 nM, more preferably <5000 nM, even more preferably <500 nM or even more preferably <100 nM.

In a particular embodiment, the compounds selected showing a binding expressed as $K_i$ which is $K_i$ (α2δ-1) >=5000 nM, show a binding, expressed as percentage of inhibition, of between 1% and 50%. The binding of the compounds, expressed as $K_i$ or as percentage of inhibition, is measured as explained in the Examples below.

In another aspect, the invention refers to a process for the preparation of a compound of formula (I) as defined above.

The obtained reaction products may, if desired, be purified by conventional methods, such as crystallization and chromatography. Where the processes described below for the preparation of compounds of the invention give rise to mixtures of stereoisomers, these isomers may be separated by conventional techniques such as preparative chromatography. The compounds may be prepared in racemic form, or individual enantiomers may be prepared either by enantiospecific synthesis or by resolution.

One preferred pharmaceutically acceptable form of a compound of the invention is the crystalline form, including such form in pharmaceutical composition. In the case of salts and also solvates of the compounds of the invention the additional ionic and solvent moieties must also be non-toxic. The compounds of the invention may present different polymorphic forms, it is intended that the invention encompasses all such forms.

The compounds of formula (I) can be obtained by following the method described below. As it will be obvious to one skilled in the art, the exact method used to prepare a given compound may vary depending on its chemical structure.

The compounds of formula (I) may be prepared by the processes as described in Scheme 1. The reactions steps are shown in Scheme 1 below in more detail. In particular, Scheme 1 shows the preparation of compounds of formula (I) wherein A is —$(CH_2)_n$—$NR_2R_2'$ and $R_1$ is hydrogen, formula (Ia):

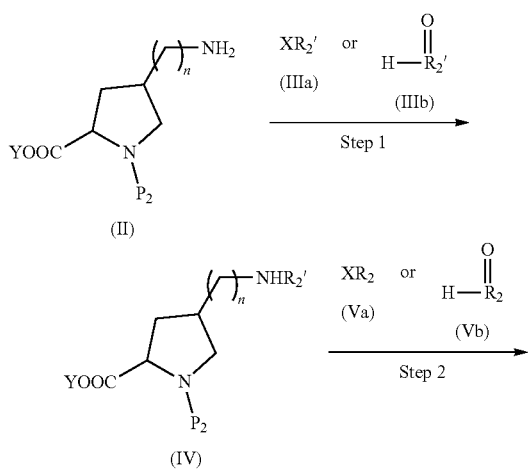

-continued

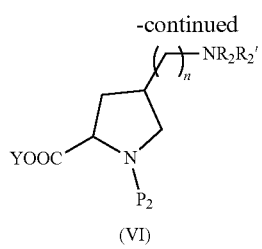

(VI)

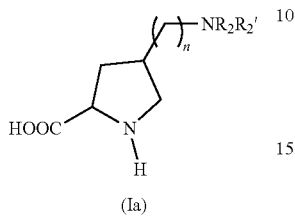

(Ia)

wherein R₁ is hydrogen and R₂ and R₂' have the same meaning as described above for a compound of formula (I), X represents a leaving group such as an halogen atom, Y represents R₁ or P₁, wherein P₁ is a suitable protecting group for the ester function, such as methyl or tert-butyl, and P₂ represents a suitable protecting group for the amino function, such as tert-butoxycarbonyl (Boc).

In this sense, in another aspect, the invention refers to a process for the preparation of a compound of formula (I) wherein A is —(CH₂)ₙ—NR₂R₂' and R₁ is hydrogen, formula (Ia):

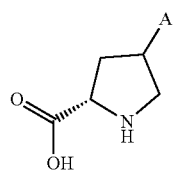

(Ia)

said process comprising a) treating a compound of formula (IV)

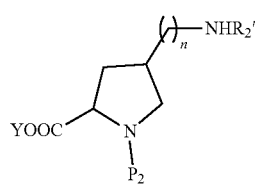

(IV)

with a compound of formula (Va) or a compound of formula (Vb)

XR₂     (Va)

or

     (Vb)

in order to obtain a compound of formula (VI)

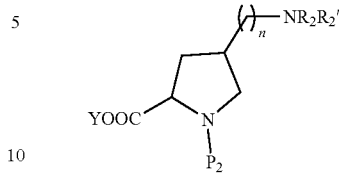

(VI)

and b) de-protecting the compound of formula (VI) obtained according to step a);

wherein R₁ is hydrogen and R₂ and R₂' have the meaning as described above for a compound of formula (I), X represents a leaving group such as an halogen atom, Y represents R₁ or P₁, wherein P₁ is a suitable protecting group for the ester function, such as methyl or tert-butyl, and P₂ represents a suitable protecting group for the amino function, such as tert-butoxycarbonyl (Boc).

According to the process of the invention, the compound of formula (I) wherein R₁ is hydrogen (Ia) can be prepared by deprotection of a compound of formula (VI). In a particular embodiment, both P₁ (if present) and P₂ protecting groups may be removed by adding a solution of a strong acid such as HCl, in a suitable solvent such as diethyl ether, 1,4-dioxane, tetrahydrofuran, water or mixtures thereof, or with trifluoroacetic acid in dichloromethane.

According to step a) of the process of the invention, in a particular embodiment, a compound of formula (VI) can be prepared by treating a compound of formula (IV), with a suitable halide of formula (Va), where X stands for halogen, in the presence of a base such as sodium hydride, in a suitable solvent, for example N,N-dimethylformamide (DMF) or THF, at a suitable temperature, such as between 0° C. and room temperature.

Alternatively, a compound of formula (VI), can be obtained by means of reductive amination reactions of a compound of formula (IV), with an aldehyde compound of formula (Vb), and using a reducing reagent, such as sodium triacetoxyborohydride, in a suitable solvent such as dichloromethane, or acetonitrile and methanol, at a suitable temperature, such as room temperature.

A compound of formula (IV) can be prepared by treating a suitable pyrrolidine-amine of formula (II) with a suitable reagent of formula (IIIa) (where X stands for halogen) or (IIIb).

Thus, in a particular embodiment, the invention refers to a process for the preparation of a compound of formula (IV) as described above in Scheme 1:

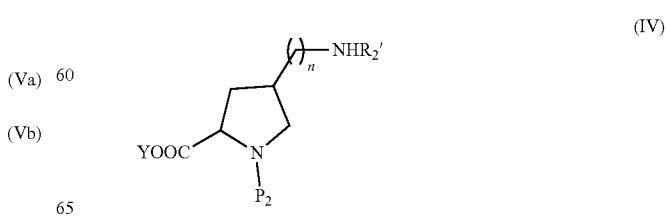

(IV)

comprising
a) treating a compound of formula (II)

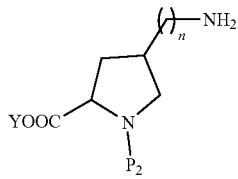
(II)

with a compound of formula (IIIa) or a compound of formula (IIIb)

XR$_2$'  or  (IIIa)

  (IIIb)

wherein R$_1$ is hydrogen, R$_2$ and R$_2$' have the meaning as described above for a compound of formula (I), X represents a leaving group such as an halogen atom, Y represents R$_1$ or P$_1$, wherein P$_1$ is a suitable protecting group for the ester function, such as methyl or tert-butyl, and P$_2$ represents a suitable protecting group for the amino function, such as tert-butoxycarbonyl (Boc).

As described above, a compound of formula (IV) can be prepared by treating a suitable pyrrolidine-amine of formula (II) with a suitable reagent of formula (IIIa) (where X stands for halogen) or (IIIb).

When a reagent of formula (IIIa) is used, the reaction is performed under Buchwald-Hartwig coupling conditions. These involve the use of suitable reagents, such as Pd$_2$(dba)$_3$ and 2-(dicyclohexylphosphino)-3,6-dimethoxy-2'-4'-6'-tri-i-propyl-1,1'-biphenyl (Brett-Phos) or 2-dicyclohexylphosphino-2',4',6'-triisopropylbiphenyl (X-Phos) in suitable solvents, such as α,α,α-trifluorotoluene or 1,4-dioxane, at a convenient temperature between 100° C. to 110° C., and optionally under microwave heating.

Alternatively, a compound of formula (IV), can be obtained by means of reductive amination reactions of a suitable amine of formula (II), with an aldehyde compound of formula IIIb, and using a reducing reagent, such as sodium triacetoxyborohydride, in a suitable solvent such as dichloromethane, or acetonitrile and methanol, at a suitable temperature, such as room temperature.

The compounds of formula (II), (III) and (V) used in the methods disclosed above are commercially available or can be synthesized following common procedures described in the literature and exemplified in the synthesis of some intermediates.

In addition, a compound of formula (I) can be obtained in enantiopure form by preforming the whole sequence described in Scheme 1 starting from enantiopure proline derivatives of formula (II). Also, an enantiopure compound can be obtained by resolution of a racemic compound of formula (I) either by chiral preparative HPLC, or by crystallization of a diastereomeric salt or co-crystal. Alternatively, the resolution step can be carried out at a previous stage, using any suitable protected intermediate.

In another aspect, the invention refers to the use of a compound selected from

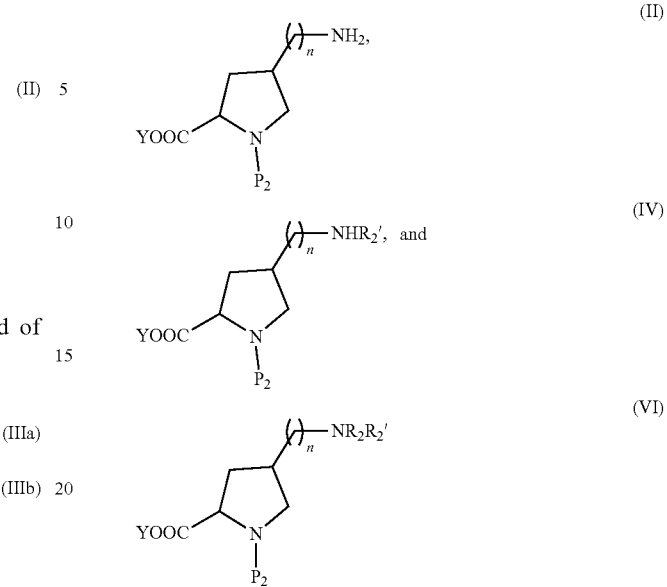

for the manufacture of a compound of formula (I), wherein R$_1$, R$_2$ and R$_2$' have the same meanings as defined above for the compound of Formula (I), X represents a leaving group such as an halogen atom, Y represents R$_1$ or P$_1$, wherein P$_1$ is a suitable protecting group for the ester function, such as methyl or tert-butyl, and P$_2$ represents a suitable protecting group for the amino function, such as tert-butoxycarbonyl (Boc).

Turning to another aspect, the invention also relates to the therapeutic use of the compounds of general formula (I). As mentioned above, compounds of general formula (I) show affinity to the subunit α2δ and more preferably to the α2δ-1 subunit of voltage-gated calcium channels and can behave as agonists, antagonists, inverse agonists, partial antagonists or partial agonists thereof. Therefore, compounds of general formula (I) are useful as medicaments.

Another aspect of the invention refers to a pharmaceutical composition which comprises a compound according to the invention as described above according to formula (I) or a pharmaceutically acceptable salt thereof, prodrug, solvate or stereoisomer thereof, and a pharmaceutically acceptable carrier, adjuvant or vehicle. The present invention thus provides pharmaceutical compositions comprising a compound of this invention, or a pharmaceutically acceptable salt, prodrug, solvate or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrups or solutions and may contain conventional excipients known in the art such as binding agents, for example syrup, acacia, gelatine, sorbitol, tragacanth, or polyvinylpyrrolidone; fillers, for example lactose, sugar, maize starch, calcium phosphate, sorbitol or glycine; tableting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling or tableting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Another aspect of the invention refers to a compound of formula (I) as described above, or a pharmaceutical acceptable salt or isomer thereof for use in therapy.

Another aspect of the invention refers to a compound of formula I, or a pharmaceutically acceptable salt or isomer thereof, for use in the treatment or prophylaxis of pain. Preferably, the pain is medium to severe pain, visceral pain, chronic pain, cancer pain, migraine, inflammatory pain, acute pain or neuropathic pain, allodynia or hyperalgesia. This may include mechanical allodynia or thermal hyperalgesia.

Another aspect of the invention refers to the use of a compound of the invention in the manufacture of a medicament for the treatment or prophylaxis of pain. In a preferred embodiment the pain is selected from medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

Another aspect of this invention relates to a method of treating or preventing pain which method comprises administering to a patient in need of such a treatment or prevention a therapeutically effective amount of a compound as above defined or a pharmaceutical composition thereof. Among the pain syndromes that can be treated or prevented are medium to severe pain, visceral pain, chronic pain, cancer pain, migraine, inflammatory pain, acute pain or neuropathic pain, allodynia or hyperalgesia, whereas this could also include mechanical allodynia or thermal hyperalgesia.

Another aspect of the invention refers to a compound of formula (I), or a pharmaceutically acceptable salt or isomer thereof, for use as neuroprotective agent.

In a more particular embodiment, the invention refers to a compound of formula I, or a pharmaceutically acceptable salt or isomer thereof, for use in the treatment or prophylaxis of neurological disorders concomitant with nervous system damage. Preferably, such neurological or nervous system disorders are polyneuropathy, motor neuron diseases or related disorders, movement disorders, disorders with neurocognitive impairment, cerebral-vascular accidents (CVAs), stroke, traumatic brain injury, spinal cord injury, multiple sclerosis or retinopathy.

The present invention is illustrated below with the aid of examples. These illustrations are given solely by way of example and do not limit the general spirit of the present invention.

EXAMPLES

In the next examples the preparation of both intermediate compounds as well as compounds according to the invention are disclosed.

The following abbreviations are used:
ACN: Acetonitrile
AcOH: Acetic acid
BrettPhos: 2-(Dicyclohexylphosphino)-3,6-dimethoxy-2'-4'-6'-tri-i-propyl-1,1'-biphenyl
DIPEA: N,N-Diisopropylethylamine
DCM: Dichloromethane
ESI: Electrospray ionization
EtOAc: Ethyl acetate
Et$_2$O: Diethyl ether
Eq. Equivalents
h: Hour/s
HPLC: High-performance liquid chromatography
LCMS: Liquid chromatography mass spectrometry
M: Molar
MeOH: Methanol
Min: Minutes
MS: Mass spectrometry
MW: microwave
Pd$_2$(dba)$_3$: tris(dibenzylideneacetone)dipalladium (0)
Py: purity
Rt: Retention time
rt: Room temperature
Sat: Saturated
t-BuOH: Tertiary butanol
TFA: Trifluoroacetic acid
THF: Tetrahydrofuran
TEA: Et$_3$N, Triethylamine
Wt: Weight
y: Yield The following methods were used to generate the LCMS data:

Method A: SC_BASE, Apparatus: Agilent 1100 Bin. Pump: G1312A, degasser; autosampler, ColCom, DAD: Agilent G1315B, 220-320 nm, MSD: Agilent LC/MSD G6130B ESI, pos/neg 100-1000; column: Waters XSelect™ CSH C18, 30×2.1 mm, 3.5µ, Temp: 25° C., Flow: 1 mL/min, Gradient: $t_0$=5% A, $t_{1.6min}$=98% A, $t_{3min}$=98% A, Posttime: 1.3 min, EluentA: acetonitrile, Eluent B: 10 mM ammoniumbicarbonate in water (pH=9.5)

Method B: SC_BASE, Apparatus: Agilent 1100 Bin. Pump: G1312A, degasser; autosampler, ColCom, DAD: Agilent G1315B, 210 nm, MSD: Agilent LC/MSD G6130B ESI, pos/neg 100-1000; column: Waters XSelect™ CSH C18, 30×2.1 mm, 3.5µ, Temp: 25° C., Flow: 1 mL/min, Gradient: $t_0$=5% A, $t_{1.6min}$=98% A, $t_{3min}$=98% A, Posttime: 1.3 min, Eluent A: acetonitrile, Eluent B: 10 mM ammoniumbicarbonate in water (pH=9.5)

Method C: AN_BASE, Apparatus: Agilent 1100 Bin. Pump: G1312A, degasser; autosampler, ColCom, DAD: Agilent G1315B, 210 nm, MSD: Agilent LC/MSD G6130B ESI, pos/neg 100-1000; column: Waters XSelect™ CSH C18, 50×2.1 mm, 3.5µ, Temp: 25° C., Flow: 0.8 mL/min, Gradient: $t_0$=5% A, $t_{3.5min}$=98% A, $t_{6min}$=98% A, Posttime: 2 min, Eluent A: acetonitrile, Eluent B: 10 mM ammoniumbicarbonate in water (pH=9.5)

Method D: SC_ACID, Apparatus: Agilent 1200 Bin. Pump: G1312A, degasser; autosampler, ColCom, DAD: Agilent G1315D, 210 nm, MSD: Agilent LC/MSD G6130B ESI, pos/neg 100-1000; ELSD Alltech 3300 gas flow 1.5 mL/min, gas temp: 40° C.; column: Waters XSelect™ CSH C18, 30×2.1 mm, 3.5µ, Temp: 35° C., Flow: 1 mL/min, Gradient: $t_0$=5% A, $t_{1.6min}$=98% A, $t_{3min}$=98% A, Posttime: 1.3 min, Eluent A: 0.1% formic acid in acetonitrile, Eluent B: 0.1% formic acid in water Method E: UPLC_AN_ACID, Apparatus: Waters IClass; Bin. Pump: UPIBSM, SM: UPISMFTN with SO; UPCMA, PDA: UPPDATC, 210-320 nm, SQD: SQD2 ESI, pos/neg 100-800; ELSD: gas pressure 40 psi, drift tube temp: 50° C.; column: Waters XSelect CSH C18, 50×2.1 mm, 2.5µ, Temp: 40° C., Flow: 0.6 mL/min, Gradient: $t_0$=5% A, $t_{2.0min}$=98% A, $t_{2.7min}$=98% A, Posttime: 0.3 min, Eluent A: 0.1% formic acid in acetonitrile, Eluent B: 0.1% formic acid in water Method F: SC_BASE, Apparatus: Agilent 1260 Bin. Pump: G1312B, degasser; autosampler, ColCom, DAD: Agilent G1315C, 210 nm, MSD: Agilent LC/MSD G6130B ESI, pos/neg 100-1000; column: Waters XSelect™ CSH C18, 30×2.1 mm, 3.5µ, Temp: 25° C., Flow: 1 mL/min, Gradient: $t_0$=5% A, $t_{1.6min}$=98% A, $t_{3min}$=98% A, Posttime: 1.3 min, Eluent A: acetonitrile, Eluent B: 10 mM ammoniumbicarbonate in water (pH=9.5)

Method G: SC_BASE, Apparatus: Agilent 1260 Bin. Pump: G1312B, degasser; autosampler, ColCom, DAD: Agilent G1315C, 210 nm, MSD: Agilent LC/MSD G6130B ESI, pos/neg 100-1000; column: Waters XSelect™ CSH C18, 30×2.1 mm, 3.5µ, Temp: 25° C., Flow: 1 mL/min, Gradient: $t_0$=5% A, $t_{1.6min}$=98% A, $t_{3min}$=98% A, Posttime: 1.3 min, Eluent A: acetonitrile, Eluent B: 10 mM ammoniumbicarbonate in water (pH=9.5)

The following methods were used to purify compounds by reverse phase (MPLC) column chromatography:

[XSelect] Instrument type: Reveleris™ prep MPLC; column: Waters XSelect CSH C18 (145×25 mm, 10ρ); Flow: 40 mL/min; Column temp: room temperature; Eluent A: 10 mM ammoniumbicarbonate in water pH=9.0); Eluent B: 99% acetonitrile+1% 10 mM ammoniumbicarbonate in water; Gradient: t=0 min 50% B, t=4 min 50% B, t=16 min 100% B, t=21 min 100% B, or Gradient: t=0 min 5% B, t=1 min 5% B, t=2 min 20% B, t=20 min 60% B, t=21 min 100% B, t=26 min 100% B; Detection UV: 220, 254, 340 nm.

[Gemini] Instrument type: Reveleris™ prep MPLC; Column: Phenomenex Gemini C18 (185×25 mm, 10ρ); Flow: 40 mL/min; Column temp: room temperature; Eluent A: 10 mM ammoniumbicarbonate in water pH=9.0); Eluent B: 99% acetonitrile+1% 10 mM ammoniumbicarbonate in water; Gradient: t=0 min 50% B, t=4 min 50% B, t=16 min 100% B, t=21 min 100% B, or Gradient: t=0 min 5% B, t=1 min 5% B, t=2 min 20% B, t=17 min 60% B, t=18 min 100% B, t=23 min 100% B; Detection UV: 220, 254, 340 nm.

Synthesis of Intermediates

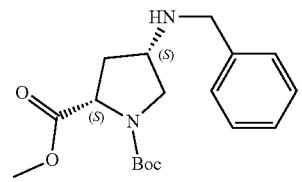

Intermediate 1. 1-(Tert-butyl) 2-methyl (2S,4S)-4-(benzylamino)pyrrolidine-1,2-dicarboxylate Intermediate 1 was prepared from 1-(tert-butyl) 2-methyl (2S,4S)-4-aminopyrrolidine-1,2-dicarboxylate hydrochloride (2.5 g, 8.90 mmol), benzaldehyde (0.906 mL, 8.90 mmol) and DIPEA (3.1 mL, 17.81 mmol, 2 eq.) in DCM (65 mL). After stirring 16 h, sodium triacetoxyborohydride (5.56 g, 26.7 mmol, 3 eq.) was added and stirring was continued for 2 h. Sat aqueous $NaHCO_3$ solution (50 mL) was added and the mixture was stirred vigorously for 30 min, after which the layers were separated (phase separator) and the organic layer was concentrated in vacuo. Purification by flash column chromatography (pre-packed silica cartridge GraceResolv™ 40 g, gradient DCM/(0-75% DCM/MeOH (9:1)) in 54 Min) afforded 1.88 g (63%) of the title compound as a colourless oil. LCMS (Method F): Rt, 2.03 Min; ESI m/z: 335.2 [M+H]$^+$.

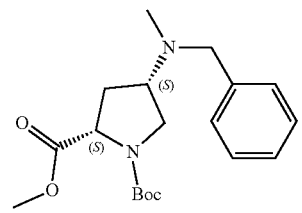

Intermediate 2. 1-(Tert-butyl)-2-methyl-(2S,4S)-4-(benzyl(methyl)amino) pyrrolidine-1,2-dicarboxylate Intermediate 2 was obtained from intermediate 1 (1.88 g, 5.65 mmol) and formaldehyde (37 wt % solution in water, 1.57 mL, 56.5 mmol, 10 eq.) in a mixture of MeOH (20 mL) and ACN (20 mL) using AcOH (0.815 mL, 14.11 mmol, 2.5 eq.) and sodium triacetoxyborohydride (2.99 g, 14.11 mmol, 2.5 eq.) according to the method for the preparation of intermediate 1. For work-up DCM (50 mL) and sat aqueous $NaHCO_3$ solution (50 mL) was used. Crude yield: 2.04 g (104%). LCMS (Method G): Rt, 2.14 Min; ESI m/z: 349.2 [M+H]$^+$.

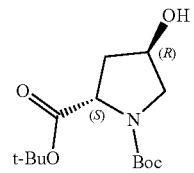

Intermediate 3. Di-tert-butyl (2S,4R)-4-hydroxypyrrolidine-1,2-dicarboxylate To a suspension of N,N'-methanediylidenebis(propan-2-amine) (88 mL, 568 mmol, 5 eq.) in t-BuOH (143 mL, 1286 mmol, 13 eq.) was added cuprous chloride (0.559 g, 5.65 mmol, 0.05 eq.). The reaction mixture was stirred at room temperature for 6 days, after which (2S,4R)-1-(tert-butoxycarbonyl)-4-hydroxypyrrolidine-2-carboxylic acid (26.2 g, 113 mmol) and DCM (230 mL) were added and the reaction mixture was stirred at room temperature for 4 days. The reaction mixture was filtered over a small pad of kieselguhr and concentrated in vacuo. Purification by column chromatography (1 kg silica, Hep/10-80% EtOAc) afforded 25.62 g of the title compound. LCMS (Method D): Rt=1.93 ESI m/z=332.2 [M+HCOO]⁻

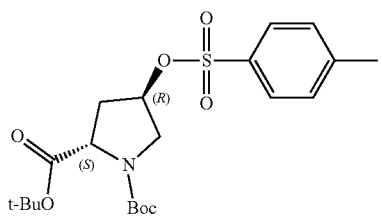

Intermediate 4. Di-tert-butyl (2S,4R)-4-(tosyloxy)pyrrolidine-1,2-dicarboxylate To a solution of intermediate 3 (24.56 g, 85 mmol) and TEA (41.0 mL, 294 mmol, 3.4 eq.) in DCM (75 mL) was added a solution of 1.8 eq. of p-toluenesulfonyl chloride (29.93 g, 157 mmol, 1.8 eq.) in DCM (75 mL). 4-Dimethylaminopyridine (0.967 g, 7.92 mmol) was added and the reaction mixture was stirred at room temperature for 16 h. The mixture was concentrated in vacuo, suspended in DCM (20 mL) and filtered over a plug of silica using Hep/EtOAc (1:1) as solvent. Additional purification by column chromatography (1 kg silica, Hep/10-80% EtOAc) afforded 32.56 g of the title compound. LCMS (Method D): Rt=2.30 ESI m/z=286.1 [M−$C_5H_8O_2$−$C_4H_8$+H]+

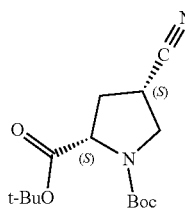

Intermediate 5. Di-tert-butyl (2S,4R)-4-cyanopyrrolidine-1,2-dicarboxylate

To a solution of intermediate 4 (12.21 g, 27.7 mmol) in DMSO (340 mL) sodium cyanide (2.98 g, 60.8 mmol, 2.2 eq.) was added. The reaction mixture was stirred at 80° C. for 16 h. Sat aqueous $NaHCO_3$ solution (110 mL), water (110 mL) and brine (110 mL) were added and the product was extracted with $Et_2O$ (6×360 mL). The organic layers were combined and concentrated in vacuo. Purification by column chromatography (gradient Hep/10-80% EtOAc) afforded 11.83 g (y: 50%, py: 81%) of the title compound. LCMS (Method B): Rt=2.27 ESI m/z=185.1 [M−2×($C_4H_8$)+H]+

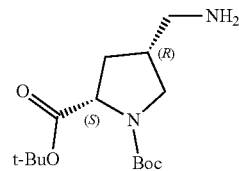

Intermediate 6. Di-tert-butyl (2S,4R)-4-(aminomethyl)pyrrolidine-1,2-dicarboxylate A solution of intermediate 5 (16.2 g, 49.5 mmol) and 7 M ammonia in methanol (49.5 mL, 346 mmol, 7 eq.) in ethanol (820 mL) was flushed with nitrogen. Raney Nickel (50% slurry in water, 5.81 g, 49.5 mmol) was added. The mixture was stirred under hydrogen atmosphere for 16 h. The mixture was filtered over a small pad of kieselguhr and concentrated in vacuo. Purification by flash column chromatography (pre-packed silica cartridge GraceResolv™ 300 g, gradient DCM/(0-5% DCM/$NH_3$ in MeOH (9:1)) in 67 Min) afforded 11.5 g (74%) of the title compound. LCMS (Method B): Rt=2.00 ESI m/z=301.2 [M+H]+

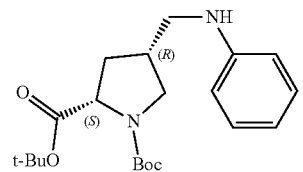

Intermediate 7. Di-tert-butyl (2S,4R)-4-((phenylamino)methyl)pyrrolidine-1,2-dicarboxylate A solution of intermediate 6 (150 mg, 0.499 mmol), bromobenzene (0.053 mL, 0.499 mmol) and sodium tert-butoxide (58 mg, 0.599 mmol, 1.2 eq.) in α,α,α-trifluorotoluene (2.5 mL) was flushed with nitrogen. BrettPhos (21.44 mg, 0.040 mmol, 0.08 eq.) and $Pd_2(dba)_3$ (9.15 mg, 0.010 mmol, 0.02 eq.) were added. The dark yellow solution was stirred at 100° C. under MW-heating (Biotage) for 1 h. After cooling down to rt the reaction mixture was filtered over a small pad of kieselguhr and concentrated in vacuo. Purification by flash column chromatography (pre-packed silica cartridge GraceResolv™ 12 g, gradient DCM/(0-100% DCM/MeOH (9:1)) in 20 Min) afforded 193 mg (95%) of the title compound as a yellow oil. LCMS (Method B): Rt=2.40 ESI m/z=377.2 [M+H]+

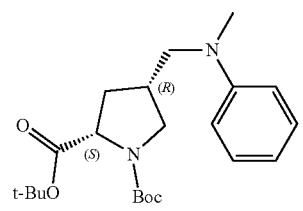

Intermediate 8. Di-tert-butyl (2S,4R)-4-((methyl (phenyl)amino)methyl)pyrrolidine-1,2-dicarboxylate Intermediate 8 was obtained by treating intermediate 7 (193 mg, 0.477 mmol), with formaldehyde (37 wt % solution in water) (0.358 mL, 4.77 mmol, 10 eq.) and AcOH (0.069 mL, 1.192 mmol, 2.5 eq.) in MeOH (2 mL)/ACN (2 mL). After stirring for 16 h, sodium triacetoxyborohydride (253 mg, 1.192 mmol, 2.5 eq.) was added, and stirring was continued for 2 h. The reaction mixture was concentrated in vacuo, dissolved in DCM (10 mL) and washed with sat aqueous NaHCO$_3$ solution (10 mL). The layers were separated (phase separator) and the organic layer was concentrated in vacuo. Purification by flash column chromatography (pre-packed silica cartridge GraceResolv™ 12 g, gradient DCM/(0-100% DCM/MeOH (9:1)) in 30 Min) afforded 94 mg (y: 44%, py: 88%) of the title compound as yellow oil. LCMS (Method A): Rt, 2.52 Min; ESI m/z: 391.2 [M+H]$^+$.

Intermediate 10. (2S,4S)-1-(Tert-butoxycarbonyl)-4-((3-chlorophenyl)(methyl)amino)pyrrolidine-2-carboxylic acid Intermediate 9 (490 mg, 0.949 mmol) was dissolved in THF (10 mL). The mixture was cooled to 0° C., sodium hydride (456 mg, 11.38 mmol, 12 eq.) was added and the suspension was stirred at room temperature for 20 min. Iodomethane (0.59 mL, 9.48 mmol, 10 eq.) was added and the mixture was stirred for 4 days. The mixture was diluted with THF (10 mL) and cooled to 0° C. Water (10 mL) was carefully added, followed by 5% aqueous citric acid (5 mL) and sat aqueous NaHCO$_3$ solution (10 mL). The layers were separated, and the aqueous layer was extracted with EtOAc (2×10 mL). The organic layers were combined and concentrated in vacuo. The aqueous layer was acidified with citric acid and extracted with EtOAc (2×20 mL). The organic layers were combined and concentrated in vacuo. The combined residues were treated with sat. aqueous NaHCO$_3$ solution (10 mL) and the mixture was extracted with Et$_2$O (10 mL). The aqueous layer was acidified with citric acid and extracted with EtOAc (2×20 mL). The EtOAc layers were combined, washed with brine and concentrated in vacuo to obtain the title compound (239 mg, y: 51, py: 73%) as a yellow oil. LCMS (Method A): Rt=1.77 ESI m/z=355.2 [M+H]$^+$, Cl-isotope pattern.

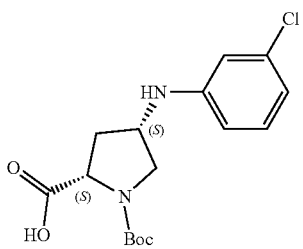

Intermediate 9. (2S,4S)-1-(Tert-butoxycarbonyl)-4-((3-chlorophenyl)amino)pyrrolidine-2-carboxylic acid A solution of N-Boc-cis-4-amino-l-proline methyl ester hydrochloride (450 mg, 1.603 mmol), 1-bromo-3-chlorobenzene (0.188 mL, 1.603 mmol) and sodium tert-butoxide (539 mg, 5.61 mmol, 3.5 eq.) in ACN (2.5 mL)/1,4-dioxane (1.5 mL) was flushed with nitrogen. BrettPhos (68.8 mg, 0.128 mmol, 0.08 eq.) and Pd$_2$(dba)$_3$ (29.4 mg, 0.032 mmol, 0.02 eq.) were added. The dark yellow solution was stirred at 100° C. under MW-heating (Biotage) for 1 h. After cooling down to rt the mixture was filtered over a small pad of kieselguhr and concentrated in vacuo to obtain 751 mg (y: 95%, py: 66%) of the title compound as a yellow oil. LCMS (Method A): Rt=1.71 ESI m/z=285.1 [M−C$_4$H$_8$+H]$^+$, Cl-isotope pattern.

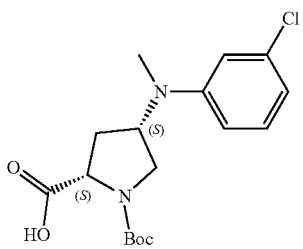

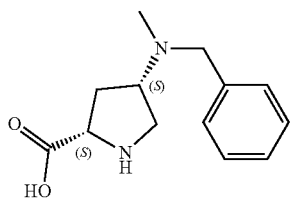

Example 1. (2S,4S)-4-(Benzyl(methyl)amino)pyrrolidine-2-carboxylic acid

Intermediate 2 (1.97 g, 5.65 mmol) was dissolved in 1 M aqueous HCl (60 mL) and the reaction mixture was stirred at 60° C. for 16 h. The reaction mixture was concentrated under reduced pressure and purified by preparative LC(MS) (XSelect CSH C18, basic eluent) to obtain the title compound (592 mg, 2.19 mmol, 39%) as a white solid. LCMS (Method E): Rt=0.94 ESI m/z=235.1 [M+H]$^+$ The method as described for the preparation of Example 1 was used for the preparation of Examples 2-6. If needed, ACN was added additionally to solubilise the starting material. Purification was performed by preparative LC(MS) (XSelect CSH C18, basic eluent):

| STRUCTURE | EX | CHEMICAL NAME | Rt time (min) | MS (M + H) | LCMS Method |
|---|---|---|---|---|---|
| 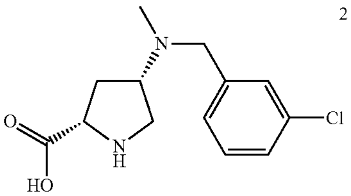 | 2 | (2S,4S)-4-((3-Chlorobenzyl)(methyl)amino)pyrrolidine-2-carboxylic acid | 3.04 | 269.1 | C |
| 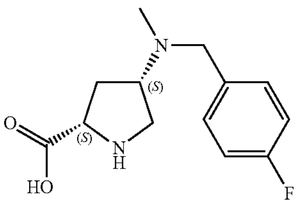 | 3 | ((2S,4S)-4-((4-Fluorobenzyl)(methyl)amino)pyrrolidine-2-carboxylic acid | 2.26 | 253.1 | C |
| 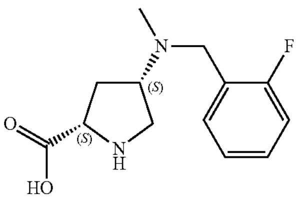 | 4 | (2S,4S)-4-((2-Fluorobenzyl)(methyl)amino)pyrrolidine-2-carboxylic acid | 2.19 | 253.1 | C |
| 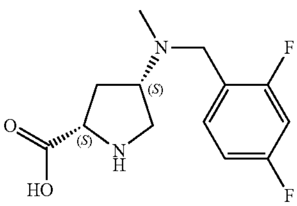 | 5 | (2S,4S)-4-((2,4-Difluorobenzyl)(methyl)amino)pyrrolidine-2-carboxylic acid | 2.28 | 271.1 | C |
| 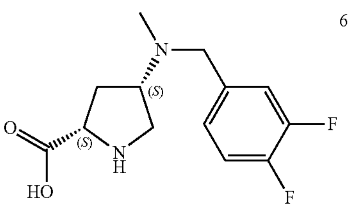 | 6 | (2S,4S)-4-((3,4-Difluorobenzyl)(methyl)amino)pyrrolidine-2-carboxylic acid | 2.36 | 271.1 | C |

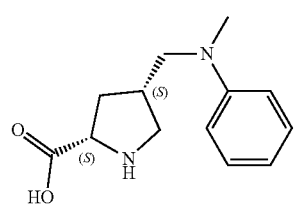

Example 7. (2S,4S)-4-((Methyl(phenyl)amino)methyl)pyrrolidine-2-carboxylic acid

Intermediate 8 (94 mg, 0.212 mmol) was dissolved in 1 M aqueous HCl (5 mL) and the reaction mixture was stirred at 60° C. for 16 hours. The reaction mixture was concentrated under reduced pressure and purified by preparative LC (XSelect CSH C18, basic eluent) to obtain the title compound (36 mg, 0.154 mmol, 73%) as a white solid.
LCMS (Method C): Rt=2.16 ESI m/z=235.1 [M+H]$^+$

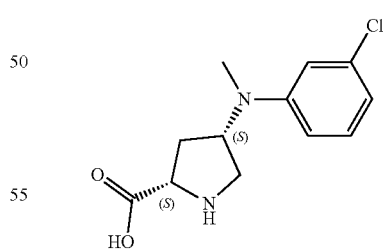

Example 8. (2S,4S)-4-((3-Chlorophenyl)(methyl)amino)pyrrolidine-2-carboxylic acid Intermediate 10 (239 mg, 0.485 mmol) was dissolved in DCM (5 mL). TFA (0.743 mL, 9.70 mmol, 20 eq.) was added and the reaction mixture was stirred at room temperature for 3 hours. The crude reaction mixture was concentrated in vacuo. Purification by preparative LC (XSelect CSH C18, basic eluent) to obtain the title compound (53 mg, 0.208 mmol, 43%) as a white solid. LCMS (Method C): Rt=1.64 ESI m/z=255.1 [M+H]$^+$, Cl-isotope pattern.

Pharmacological Study

This invention is aimed at providing a series of compounds which show pharmacological activity towards the subunit α2δ of voltage-gated calcium channels (VGCC), especially the α2δ-1 subunit of voltage-gated calcium channels and especially compounds which have a binding expressed as $K_i$ responding to the following scales:

$K_i$(α$_2$δ-1) is preferably <10000 nM, more preferably <5000 nM, even more preferably <500 nM and even more preferably <100 nM.

Human α2δ-1 Subunit of Ca$_v$2.2 Calcium Channel Assay

Human α2δ-1 enriched membranes (2.5 μg) were incubated with 15 nM of radiolabeled [3H]-Gabapentin in assay buffer containing Hepes-KOH 10 mM, pH 7.4.

NSB (non specific binding) was measured by adding 10 μM pregabalin. The binding of the test compound was measured at either one concentration (% inhibition at 1 μM or 10 M) or five different concentrations to determine affinity values ($K_i$). After 60 min incubation at 27° C. binding reaction was terminated by filtering through Multiscreen GF/C (Millipore) presoaked in 0.5% polyethyleneimine in Vacuum Manifold Station, followed by 3 washes with ice-cold filtration buffer containing 50 mM Tris-HCl, pH 7.4. Filter plates were dried at 60° C. for 1 hour and scintillation cocktail (30 μL) were added to each well before radioactivity reading. Readings were performed in a Trilux 1450 Microbeta radioactive counter (Perkin Elmer).

Results:

All compounds of the invention (Examples 1-8) show a $K_i$(α$_2$δ-1)<100 nM.

The invention claimed is:

1. A compound of formula (I):

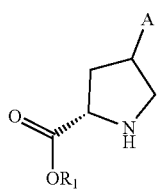

(I)

a stereoisomer thereof, or a corresponding salt thereof, or a corresponding solvate thereof, wherein
R$_1$ is selected from the group consisting of hydrogen, unsubstituted or substituted C$_{1-6}$ alkyl, substituted or unsubstituted C$_{2-6}$ alkenyl, and substituted or unsubstituted C$_{2-6}$ alkynyl;
A is —(CH$_2$)$_n$—NR$_2$R$_2$', wherein n is 0, 1 or 2;
R$_2$ is unsubstituted C$_{1-6}$ alkyl; and
R$_2$' is —(CH$_2$)$_m$—R$_3$, wherein
m is 0, 1, 2 or 3;
R$_3$ is selected from the group consisting of unsubstituted or substituted aryl, unsubstituted or substituted cycloalkyl, and unsubstituted or substituted heterocyclyl, wherein the heterocyclyl is not a sulfur-containing heterocyclyl.

2. The compound according to claim 1, wherein R$_1$ is hydrogen.

3. The compound according to claim 1, wherein n is 0 or 1.

4. The compound according to claim 1, wherein R$_2$ is unsubstituted C$_{1-3}$ alkyl.

5. The compound according to claim 1, wherein m is 0 or 1.

6. The compound according to claim 1, wherein R$_3$ is unsubstituted or substituted aryl.

7. The compound according to claim 1, when the aryl, heterocyclyl or cycloalkyl in R$_3$ is substituted, the substituents are selected from halogen, unsubstituted C$_{1-6}$ alkyl, —OR', —SR', —SOR', —SO$_2$R', —CN, —COR', —COOR', haloalkyl, haloalkoxy or —OC$_{1-6}$ alkyl wherein R' is selected from the group consisting of hydrogen, OH and unsubstituted C$_{1-6}$ alkyl.

8. The compound according to claim 1 wherein said compound is selected from the group consisting of:
(2S,4S)-4-(Benzyl(methyl)amino)pyrrolidine-2-carboxylic acid;
(2S,4S)-4-((3-Chlorobenzyl)(methyl)amino)pyrrolidine-2-carboxylic acid;
(2S,4S)-4-((4-Fluorobenzyl)(methyl)amino)pyrrolidine-2-carboxylic acid;
(2S,4S)-4-((2-Fluorobenzyl)(methyl)amino)pyrrolidine-2-carboxylic acid;
(2S,4S)-4-(2,4-Difluorobenzyl)(methyl)amino)pyrrolidine-2-carboxylic acid;
(2S,4S)-4-((3,4-Difluorobenzyl)(methyl)amino)pyrrolidine-2-carboxylic acid;
(2S,4S)-4-((Methyl(phenyl)amino)methyl)pyrrolidine-2-carboxylic acid; and
(2S,4S)-4-((3-Chlorophenyl)(methyl)amino)pyrrolidine-2-carboxylic acid.

9. A process for the preparation of a compound of formula (I) wherein R$_1$ is hydrogen (Ia) said process comprising:

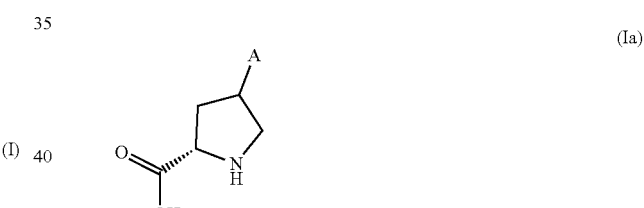

(Ia)

a) treating a compound of formula (IV)

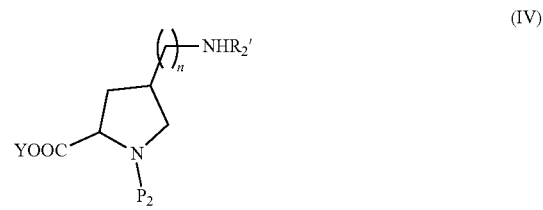

(IV)

with a compound of formula (Va) or a compound of formula (Vb)

XR$_2$ or (Va)

$$H-\overset{O}{\underset{\|}{C}}-R_2$$

(Vb)

in order to obtain a compound of formula (VI)

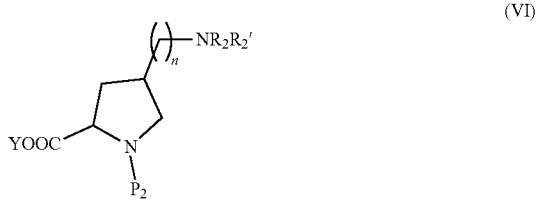

and b) de-protecting the compound of formula (VI) obtained according to step a);

wherein $R_1$, $R_2$ and $R_2'$ have the same meaning as indicated in claim 1, X represents a leaving group, Y represents $R_1$ or $P_1$, wherein $P_1$ is a suitable protecting group, and $P_2$ represents a suitable protecting group for the amino function.

10. A pharmaceutical composition comprising a compound of claim 1.

11. A method for treating a disease or a disorder mediated by a subunit α δ said method comprising administering to a subject in need of such a treatment a compound of claim 1.

12. The method according to claim 11, wherein the disease or disorder comprises pain, depression, anxiety, or attention-deficit-/hyperactivity disorder (ADHD).

13. The method according to claim 10, wherein said compound is used as a neuroprotective agent.

14. The method according to claim 13, wherein said compound is used in the treatment of a neurological disorder concomitant with nervous system damage such as polyneuropathy, motor neuron diseases, movement disorders, disorders with neurocognitive impairment, cerebral-vascular accidents (CVAs), stroke, traumatic brain injury, spinal cord injury, multiple sclerosis or retinopathy.

15. A pharmaceutical composition comprising a compound according to claim 1 or a pharmaceutically acceptable salt, a stereoisomer, prodrug, or solvate thereof, and at least a pharmaceutically acceptable carrier, additive, adjuvant, or vehicle.

16. The compound of claim 1, wherein said compound of formula (I) comprises an enantiomer, a diastereomer, or a racemic mixture.

17. The compound of claim 1, wherein said compound of formula (I) comprises an enantiomer or a diastereomer.

18. The compound of claim 1, wherein said compound of formula (I) comprises an enantiomically enriched mixture or a diastereomerically enriched mixture.

19. The method of claim 11, wherein said subunit α δ comprises a α δ-1 subunit of voltage-gated calcium channels.

20. The method of claim 12, wherein said pain comprises neuropathic pain, inflammatory pain, chronic pain, or other pain conditions involving allodynia or hyperalgesia or a combination thereof.

* * * * *